United States Patent [19]

Cherpeck

[11] Patent Number: 5,306,315

[45] Date of Patent: Apr. 26, 1994

[54] POLY(ALKYLENE ETHER) AMINES AND FUEL COMPOSITIONS CONTAINING THE SAME

[75] Inventor: Richard E. Cherpeck, Cotati, Calif.

[73] Assignee: Chevron Research and Technology Company, San Francisco, Calif.

[21] Appl. No.: 41,071

[22] Filed: Apr. 1, 1993

[51] Int. Cl.$^5$ .................. C10L 1/22; C07C 215/00
[52] U.S. Cl. ............................ 44/424; 4/425; 4/433; 4/434; 564/443; 564/461; 564/462; 564/505
[58] Field of Search ............... 44/434, 433, 425, 414; 564/443, 461, 462, 505

[56] References Cited

U.S. PATENT DOCUMENTS

| | | | |
|---|---|---|---|
| 3,440,029 | 4/1969 | Little et al. | 44/75 |
| 4,247,301 | 1/1981 | Honnen | 44/63 |
| 4,332,595 | 6/1982 | Herbstman et al. | 44/72 |
| 4,526,587 | 7/1985 | Campbell | 564/505 |
| 4,527,996 | 7/1985 | Campbell | 44/72 |
| 4,604,103 | 8/1986 | Campbell | 44/72 |
| 5,094,667 | 3/1992 | Schilowitz et al. | 44/434 |
| 5,112,364 | 5/1992 | Rath et al. | 44/418 |
| 5,192,335 | 3/1993 | Cherpeck | 44/387 |

FOREIGN PATENT DOCUMENTS 0181140 10/1985 European Pat. Off. .
0310875 9/1988 European Pat. Off. .

OTHER PUBLICATIONS

A. Verma et al., *Preparation of Poly(alkyl vinyl ether) Oligomers with Functionalized Endgroups*, Polymer Preprints, 32, pp. 322–323, (1991).

C. G. Cho et al., *Synthesis of Amine Terminated Poly(Alkyl Vinyl Ethers)*, Polymer Preprints, 28, pp. 356–357, (1987).

M. Miyamoto, et al., *Synthesis of Telechelic Living Poly(vinyl ethers)*, Macromolecules, vol. 18, No. 2, (1985).

M. Sawamoto, et al., *End-Functionalized Polymers by Living Cationic Polymerization 3.Ring-Substituted Anilines as Functional End-Capping Agents for the Synthesis of Poly(Isobutyl Vinyl Ether) with a Terminal Amine, Carboxylic Acid, or Ester Group*, Polymer Bulletin, 18, pp. 117–122, (1987).

T. Hashimoto, *End-Functionalized Polymers by Living Cationic Polymerization, IV. Poly(vinyl Ethers) with Acidic or Basic Terminal Groups by Functional Initiator Method*, Journal of Polymer Science: Part A: Polymer Chemistry, vol. 28, pp. 1137–1148 (1990).

*Primary Examiner*—Margaret Medley
*Attorney, Agent, or Firm*—Claude J. Caroli; J. A. Hagenah

[57] ABSTRACT

Poly(alkylene ether) amines having the formula:

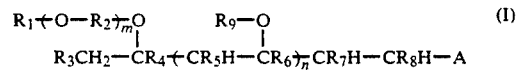

wherein A is an amine moiety having at least one basic nitrogen atom; $R_1$ is a hydrocarbyl group having a sufficient number of carbon atoms to render the poly(vinyl ether) amine soluble in hydrocarbons boiling in the gasoline or diesel fuel range; $R_2$ is an alkylene group having 2 to about 8 carbon atoms; $R_3$, $R_4$, $R_5$, $R_6$, $R_7$ and $R_8$ are each independently hydrogen or a lower alkyl group having 1 to about 4 carbon atoms; $R_9$ is an alkyl group having 1 to about 10 carbon atoms; m is 0 or 1; and n is an integer from 5 to 99. The poly(vinyl ether) amines of formula I are useful as fuel additives for the prevention and control of engine deposits.

37 Claims, No Drawings

POLY(ALKYLENE ETHER) AMINES AND FUEL COMPOSITIONS CONTAINING THE SAME

BACKGROUND OF THE INVENTION

1. Field of the Invention

This invention relates to novel end-functionalized poly(vinyl ethers). More particularly, this invention relates to novel poly(vinyl ether) amines and their use in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

Deposit control additives, however, differ in their effectiveness for preventing or controlling deposits on various engine components. This is believed to be due primarily to the fact that each engine component has a different operating temperature and some deposit control additives are not sufficiently stable on the surface of certain engine components to perform their intended function. In this regard, deposits on intake valves are particularly difficult to control, since intake valve operating temperatures can exceed 300° C. At such high temperatures, many fuel additives are too volatile to be effective, while others thermally decompose.

Therefore, it would be particularly desirable to provide effective deposit control additives which have improved thermal stability at normal engine intake valve operating temperatures and which further have a sufficient molecular weight so as to be nonvolatile at such temperatures. The present invention discloses a new class of poly(vinyl ether) amine fuel additives having such properties.

Polyether fuel additives are well known in the art. These prior art additives, however, have a poly(oxyalkylene) "backbone", i.e. the polyether portion of the molecule consists of repeating oxyalkylene units, i.e. [—CHR—CHR—O—]$_x$. In contrast, the fuel additives of the present invention have a vinyl ether polymer backbone consisting of repeating vinyl ether units, i.e. [—CHR—CR(OR)—]$_x$.

U.S. Pat. No. 4,247,301, issued Jan. 27, 1981 to L. R. Honnen, for example, discloses hydrocarbyl poly(oxyalkylene) polyamine fuel additives having a hydrocarbyl-terminated poly(oxyalkylene) chain bonded through the terminal carbon atom to a nitrogen atom of a polyamine. These additives, when added to hydrocarbon fuels, are taught to maintain the cleanliness of intake systems without contributing to combustion chamber deposits.

Similar hydrocarbyl-terminated poly(oxyalkylene) amines and fuel compositions containing such additives are described in U.S. Pat. Nos. 3,440,029; 4,332,595; 4,604,103, 5,094,667, 5,112,364; and European Patent Application Nos. 181,140; and 310,875. The fuel additives described in these patents or patent applications each have a poly(oxyalkylene) backbone.

Additionally, U.S. Pat. No. 4,527,996, issued Jul. 9, 1985 to C. B. Campbell, discloses hydroxy-terminated poly(oxyalkylene) amines and polyamines useful for maintaining the cleanliness of engine intake systems.

End-functionalized poly(vinyl ethers) are also known in the art. For example, A. Verma et al. in *Polymer Preprints*, 1991, 32, 322, describe the synthesis and characterization of functionalized poly(butyl vinyl ether) oligomers having an aldehyde or a primary hydroxyl endgroup. These poly(vinyl ethers) are prepared by the living polymerization of butyl vinyl ether using a hydrogen iodide/zinc iodide initiating system. The polymerization reaction is terminated with aqueous potassium carbonate to form the aldehyde endgroup, which can subsequently be reduced to form the primary hydroxyl endgroup.

Poly(vinyl ethers) having amine end-groups are also known. C. G. Cho et al., *Polymer Preprints*, 1987, 28, 356, describe the synthesis of amine-terminated poly(alkyl vinyl ethers) by quenching the living polymerization of alkyl vinyl ethers with p-methyl styrene and an amine. The resulting poly(alkyl vinyl ether) is covalently linked to the amine through a p-methyl styrenic unit.

M. Miyamoto et al., *Macromolecules*, 1985, 18, 123, describe the synthesis of poly(vinyl ethers) having a terminal amine group by quenching the living polymerization reaction of vinyl ether monomers with aliphatic amines. The resulting poly(vinyl ether) amines have an α-amino ether endgroup.

Similarly, M. Sawamoto et al., *Polymer Bulletin*, 1987, 18, 117, describes quenching vinyl ether polymerization reactions with anilines to form aniline-terminated poly(vinyl ethers).

Amine-terminated poly(isobutyl vinyl ethers) having a primary amine at the beginning of the vinyl ether polymer are described by T. Hashimoto et al. in *J. Poly. Sci. Polym. Chem. Ed.*, 1990, 28, 1137. These poly(vinyl ethers) are prepared by initiating the living polymerization of isobutyl vinyl ether with 2-(vinyloxy)ethyl phthalimide. The phthalimide group is then removed with hydrazine to produce a poly(isobutyl vinyl ether) having a 2-aminoethyl ether moiety on the first vinyl ether unit of the polymer.

It has now been discovered that the thermal stability of polyether fuel additives can be substantially improved by replacing the poly(oxyalkylene) component of such additives with a poly(vinyl ether) component. The resulting poly(vinyl ether) amines are surprisingly effective for controlling fuel system deposits, particularly intake valve deposits.

SUMMARY OF THE INVENTION

The present invention provides novel poly(vinyl ether) amine fuel additives which are useful for the prevention and control of engine deposits, particularly intake valve deposits.

The poly(vinyl ether) amines of the present invention have the formula:

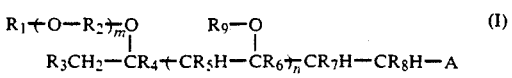
(I)

wherein A is an amine moiety having at least one basic nitrogen atom; $R_1$ is a hydrocarbyl group having a sufficient number of carbon atoms to render the poly(vinyl ether) amine soluble in hydrocarbons boiling in the gasoline or diesel fuel range; $R_2$ is an alkylene group having 2 to about 8 carbon atoms; $R_3$, $R_4$, $R_5$, $R_6$, $R_7$ and $R_8$ are each independently hydrogen or a lower alkyl group having 1 to about 4 carbon atoms; $R_9$ is an alkyl group having 1 to about 10 carbon atoms; m is 0 or 1; and n is an integer from 5 to 99.

The present invention further provides a fuel composition comprising a major amount of hydrocarbons boiling in the gasoline or diesel range and an effective deposit-controlling amount of a poly(vinyl ether) amine of the present invention.

The present invention additionally provides a fuel concentrate comprising an inert stable oleophilic organic solvent boiling in the range of from about 150° F. to 400° F. and from about 10 to 70 weight percent of a poly(vinyl ether) amine of the present invention.

The present invention also provides a method for reducing engine deposits in an internal combustion engine comprising operating the engine with the aforementioned fuel composition containing an effective deposit-controlling amount of a poly(vinyl ether) amine of the present invention.

Among other factors, the present invention is based on the surprising discovery that fuel additives having a poly(vinyl ether) backbone have improved thermal stability and provide superior control of deposits, particularly on intake valves.

DETAILED DESCRIPTION OF THE INVENTION

The fuel additives provided by the present invention have the general formula:

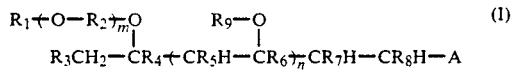   (I)

wherein A, $R_1$–$R_8$, m and n are as defined hereinabove.

A is preferably an amine moiety derived from ammonia, a monoamine having 1 to about 8 carbon atoms, or a polyamine containing 2 to about 12 amine nitrogen atoms and from 2 to about 40 carbon atoms. More preferably, A is an amine moiety derived from ammonia or a polyalkylene polyamine containing 2 to about 12 nitrogen atoms and 2 to about 24 carbon atoms. Still more preferably, A is a polyamine moiety derived from a polyalkylene polyamine having the formula:

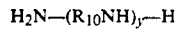

wherein $R_{10}$ is alkylene having 2 to about 6 carbon atoms and y is an integer from 1 to 3.

Preferably, $R_1$ is a hydrocarbyl group having at least 5 carbon atoms. More preferably, $R_1$ is a hydrocarbyl group having about 8 to about 120 carbon atoms. In a particularly preferred embodiment of the present invention, $R_1$ is alkyl having 8 to about 120 carbon atoms or alkylphenyl having an alky group containing 4 to about 100 carbon atoms. More preferably, $R_1$ is alkyl having 10 to 30 carbon atoms or alkylphenyl having an alkyl group containing 4 to 30 carbon atoms. Still more preferably, $R_1$ is alkylphenyl having an alkyl group containing 12 to 24 carbon atoms.

$R_2$ is preferably alkylene having 2 to 4 carbon atoms. More preferably, $R_2$ is ethylene, i.e. $-CH_2CH_2-$.

Preferably, $R_3$, $R_4$, $R_5$, $R_6$, $R_7$ and $R_8$ are each independently hydrogen, methyl or ethyl. More preferably, $R_3$, $R_4$, $R_5$, $R_6$, $R_7$ and $R_8$ are each independently hydrogen or methyl. Most preferably, $R_3$, $R_4$, $R_5$, $R_6$, $R_7$ and $R_8$ are hydrogen.

$R_9$ is preferably alkyl having 1 to 6 carbon atoms. More preferably, $R_9$ is alkyl having 2 to 4 carbon atoms.

Preferably, m is 1. Preferably, n is an integer from 10 to 50. More preferably, n is an integer from 15 to 30.

A preferred group of poly(vinyl ether) amines are those of formula I wherein A is derived from ammonia or a polyalkylene polyamine containing 2 to about 12 nitrogen atoms and 2 to about 24 carbon atoms; $R_1$ is alkyl having 8 to about 120 carbon atoms or alkylphenyl having an alkyl group containing 4 to about 100 carbon atoms; $R_2$ is alkylene having 2 to 4 carbon atoms; $R_3$, $R_4$, $R_5$, $R_6$, $R_7$ and $R_8$ are each independently hydrogen, methyl or ethyl; $R_9$ is alkyl having 1 to 6 carbon atoms; m is 0 or 1; and n is an integer from 10 to 50.

A more preferred group of poly(vinyl ether) amines are those of formula 1 wherein A is derived from a polyalkylene polyamine having the formula:

wherein $R_{10}$ is alkylene having 2 to about 6 carbon atoms and y is an integer from 1 to 3; $R_2$ is alkyl having 10 to 30 carbon atoms or alkylphenyl having an alkyl group containing 10 to 30 carbon atoms; $R_2$ is ethylene; $R_3$, $R_4$, $R_5$, $R_6$, $R_7$ and $R_8$ are each hydrogen; $R_9$ is alkyl having 2 to 4 carbon atoms; m is 0 or 1; and n is an integer from 10 to 50.

A particularly preferred group of poly(vinyl ether) amines are those having the formula:

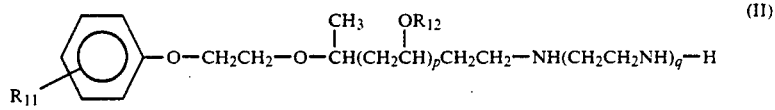   (II)

wherein $R_{11}$ is alkyl having 10 to 30 carbon atoms, $R_{12}$ is alkyl having 2 to 4 carbon atoms, p is an integer from 10 to 50, and q is an integer from 1 to 3.

The poly(vinyl ether) amines of the present invention will generally have a sufficient molecular weight so as to be non-volatile at normal engine intake valve operating temperatures. Typically, the molecular weight of the poly(vinyl ether) amines of this invention will range from about 600 to about 10,000, preferably from 1,000 to 3,000.

DEFINITIONS

As used herein the following terms have the following meanings unless expressly stated to the contrary.

The term "hydrocarbyl" refers to an organic radical primarily composed of carbon and hydrogen which may be aliphatic, alicyclic, aromatic or combinations thereof (e.g. aralkyl or alkaryl). Such hydrocarbyl groups are generally relatively free of aliphatic unsaturation, i.e. olefinic or acetylenic unsaturation, but may contain minor amounts of heteroatoms, such as oxygen or nitrogen, or halogens, such as chlorine.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl and the like.

The term "alkylene" refers to straight- and branched-chain alkylene groups having at least 2 carbon atoms. Typical alkylene groups include, for example, ethylene (—CH$_2$CH$_2$—), propylene (—CH$_2$CH$_2$CH$_2$—), isopropylene (—CH(CH$_3$)CH$_2$—), n-butylene (—CH$_2$CH$_2$CH$_2$CH$_2$—), sec-butylene (—CH(CH$_2$CH$_3$)CH$_2$—) and the like.

The term "vinyl ether" refers to an α,β-unsaturated ether having the general formula:

wherein $R_a$ and $R_b$ are generally hydrogen or lower alkyl groups; and $R_c$ is a hydrocarbyl group. The term "alkyl vinyl ether" refers to a vinyl ether in which the hydrocarbyl group, $R_c$, is an alkyl group.

The term "poly(vinyl ether)" refers to a vinyl ether polymer having the general formula:

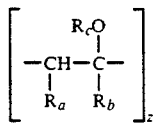

wherein $R_a$, $R_b$ and $R_c$ are as defined above and z is an integer greater than 1. The term "vinyl ether unit" refers to one monomeric unit of a poly(vinyl ether) polymer. When referring herein to the number of vinyl ether units in a particular poly(vinyl ether) compound, it is to be understood that this number refers to the average number of vinyl ether units in such compounds unless expressly stated to the contrary.

GENERAL SYNTHETIC PROCEDURES

The poly(vinyl ether) amines of this invention may be prepared by the following general methods and procedures. It should be appreciated that where typical or preferred process conditions (e.g. reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The poly(vinyl ether) amines of the present invention contain (a) a poly(vinyl ether) component and (b) an amine component.

A. The Poly(Vinyl Ether) Component

The poly(vinyl ether) component of the poly(vinyl ether) amines of the present invention is a vinyl ether polymer containing about 6 to about 100 vinyl ether units, including a hydrocarbyl vinyl ether unit and about 5 to about 99 alkyl vinyl ether units. Generally, the poly(vinyl ether) component will have a hydrocarbyl vinyl ether unit at the beginning of the vinyl ether polymer and will be terminated with a branched or unbranched ethylene group containing 2 to about 10 carbon atoms which is covalently-linked to the amine component.

The poly(vinyl ether) component of the poly(vinyl ether) amines of this invention is preferably prepared by polymerizing certain defined vinyl ether monomers under "living polymerization" conditions. The term "living polymerization" is well known in the art and refers to polymerization reactions which occur in the substantial absence of chain transfer and termination reactions. Under such conditions, the reactive end of the growing polymer is essentially stable indefinitely. Accordingly, each vinyl ether monomer can be added sequentially to the growing poly(vinyl ether) chain in a controlled step-by-step manner. Thus, living polymerization allows poly(vinyl ethers) to be prepared having a substantially predictable sequence of vinyl ether units.

In a preferred method of synthesizing the poly(vinyl ether) amines of the present invention, the living polymerization reaction is initiated using a hydrocarbyl vinyl ether monomer. Alkyl vinyl ether monomers are then added sequentially in an amount sufficient to produce the desired number of vinyl ether units. The reaction is then quenched under suitable aqueous conditions to form a carbonyl-terminated poly(vinyl ether) and the carbonyl group of the polymer is reduced to form a hydroxyl group. The resulting hydroxy-terminated poly(vinyl ether) is then coupled to the amine component by converting the hydroxyl group into a suitable leaving group and subsequently displacing the leaving group with the amine component to form the poly(vinyl ether) amines of the present invention, as described in further detail below.

The Hydrocarbyl Vinyl Ether Monomer

As indicated above, the poly(vinyl ether) amines of the present invention contain a hydrocarbyl ether moiety having a sufficient number of carbon atoms to render the poly(vinyl ether) amine soluble in hydrocarbons boiling in the gasoline or diesel fuel range. This solubility condition is satisfied if the poly(vinyl ether) amine is soluble in hydrocarbon fuel at least to the extent of about 50 parts per million by weight.

Typically, the hydrocarbyl ether moiety will contain at least about 5 carbon atoms, preferably about 8 to about 120 carbon atoms, and more preferably 10 to 36 carbon atoms.

The hydrocarbyl ether moiety of the poly(vinyl ether) amines of this invention is generally introduced into the poly(vinyl ether) component by employing a hydrocarbyl vinyl ether monomer to initiate or begin the living polymerization reaction. Suitable hydrocarbyl vinyl ether monomers have the formula:

$$R_1—(O—R_2)_m—O—C(R_4)=CHR_3 \qquad (III)$$

wherein $R_1$-$R_4$ and m are as defined above.

The hydrocarbyl vinyl ethers of formula III where m is 0 may be conveniently prepared from a monohydroxy compound and an olefin as represented by the reaction:

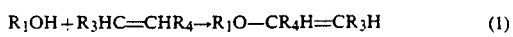
$$R_1OH + R_3HC=CHR_4 \rightarrow R_1O—CR_4H=CR_3H \qquad (1)$$

wherein $R_1$, $R_3$ and $R_4$ are as defined above. This reaction is catalyzed with a Group VIII noble metal compound, such as platinum and palladium chloride, and requires a regenerative oxidant capable of maintaining the noble metal in oxidized form, such as cupric chloride. The reaction conditions are further described in U.S. Pat. Nos. 4,057,575 and 4,161,610, both to D. L. Klass, the disclosures of which are incorporated herein by reference.

Alternatively, the hydrocarbyl vinyl ethers of formula III where m is 0 can be prepared by a vinyl exchange reaction.

Vinyl ethers and esters readily exchange their vinyl groups with hydroxy compounds in presence of a catalyst, such as palladium or mercury salts, according to the reaction:

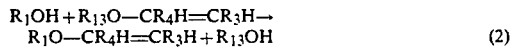
$$R_1OH + R_{13}O\text{—}CR_4H\text{=}CR_3H \rightarrow$$
$$R_1O\text{—}CR_4H\text{=}CR_3H + R_{13}OH \quad (2)$$

wherein $R_1$, $R_3$ and $R_4$ are as defined above and $R_{13}$ is a lower alkyl group, such as methyl, ethyl and the like, or an acyl group, such as acetate. Generally, an excess of the vinyl ether being used to donate the vinyl group is employed in these reactions. Suitable conditions for vinyl exchange reactions are well known in the art. For example, the palladium catalyzed reaction is described further in Japanese Patent Application No. Sho 49-43909, published Apr. 25, 1974 by K. Takagi et al., and the mercury catalyzed reaction is described by M. F. Shostakovshii et al. in *Russian Chemical Reviews*, 37, 907 (1968) and references cited therein.

Especially preferred hydrocarbyl vinyl ether monomers for use in the present invention are those of formula III where m is 1. These monomers can be conveniently prepared by reacting a monohydroxy compound, $R_1OH$ or a suitable salt thereof, with a haloalkyl vinyl ether having the formula:

$$Y\text{—}R_2\text{—}O\text{—}C(R_3)\text{=}CHR_4 \quad (IV)$$

wherein $R_2$, $R_3$ and $R_4$ are as defined above and Y is a halogen, such as chloride, bromide or iodide. Preferably, $R_3$ and $R_4$ are hydrogen and $R_2$ is an alkylene group containing 2 to 4 carbon atoms. Most preferably, $R_2$ is ethylene (—$CH_2CH_2$—) and Y is chloride.

Exemplary haloalkyl vinyl ethers include 2-chloroethyl vinyl ether, 2-chloroethyl propenyl ether, 3-bromo-n-propyl vinyl ether, and 4-chloro-n-butyl vinyl ether and the like. Some of these haloalkyl vinyl ethers are commercially available, such as 2-chloroethyl vinyl ether, which may be purchased from Aldrich Chemical Company, Inc., Milwaukee, Wis. 53233. Others can be readily prepared by the procedures described by M. F. Shostakovshii et al. in *Russian Chemical Reviews*, 37, 913–914 (1968) and references cited therein.

The reaction of a monohydroxy compound, $R_1OH$ or a suitable salt thereof, with a haloalkyl vinyl ether of formula IV is typically conducted by contacting the monohydroxy reactant with about 1.0 to about 2.0 molar equivalents of the haloalkyl vinyl ether in an inert solvent, such as dimethylformamide (DMF), dimethyl sulfoxide (DMSO) and the like, at a temperature ranging from about 30° C. to about 120° C. for about 1 to about 24 hours. Under these conditions, the monohydroxy compound, $R_1OH$, substantially displaces the halogen forming the desired hydrocarbyl vinyl ether monomers of formula III wherein m is 1. Preferably, a salt of the monohydroxy compound, such as the sodium, potassium or magnesium salt, is prepared prior to reaction with the haloalkyl vinyl ether by procedures which are well known in the art. For example, the salt of a monohydroxy alcohol can be prepared by contacting the alcohol with sodium or potassium metal, or sodium or potassium hydride in an inert solvent. Alternatively, the salt of an alkylphenol can preferably be prepared by contacting the phenol with sodium or potassium hydroxide in an inert solvent.

The monohydroxy compound $R_1OH$, used in the above reactions, is preferably a straight- or branched-chain aliphatic alcohol having 8 to about 120 carbon atoms, more preferably 10 to 30 carbon atoms; or an alkylphenol having an alkyl substituent containing about 4 to about 100 carbon atoms, more preferably 10 to 30 carbon atoms, still more preferably 12 to 24 carbon atoms.

Preferred straight-chain alcohols have about 8 to about 30 carbon atoms and include, for example, octanol, nonanol, decanol, hexadecanol (cetyl alcohol), octadecanol (stearyl alcohol) and the like. Particularly preferred straight-chain alcohols are those derived from linear $C_{10}$ to $C_{30}$ alpha olefins and mixtures thereof.

Preferred branched-chain alcohols include those derived from polymers of $C_2$ to $C_6$ olefins, such as alcohols derived from polypropylene and polybutene. Particularly preferred are polypropylene alcohols having 9 to about 60 carbon atoms and polybutene alcohols having 8 to about 120 carbon atoms. Alcohols derived from the alpha olefin oligomers of $C_8$ to $C_{16}$ alpha olefins, such as the dimer, trimer and tetramer of decene as described in U.S. Pat. No. 4,045,508, issued Aug. 30, 1977 to B. L. Cupples et al., are also useful in this invention.

Many of these straight- and branched-chain alcohols are commercially available and the others can be readily prepared from the corresponding olefins by conventional procedures. Suitable procedures for preparing alcohols from olefins are described for example in I. T. Harrison and S. Harrison, *Compendium of Organic Synthetic Methods*, pp. 119–122, Wiley-Interscience, New York (1971) and references cited therein.

In an especially preferred embodiment of the present invention, the monohydroxy compound, $R_1OH$, used to prepare the hydrocarbyl vinyl ether monomers of formula III, is an alkylphenol having the formula:

(V)

wherein $R_{14}$ is a straight- or branched-chain alkyl group having about 4 to about 100 carbon atoms, preferably 10 to 30 Carbon atoms, more preferably 12 to 24 carbon atoms; and v is 1 or 2, preferably 1.

When v is one, the alkylphenol of formula V is a monoalkylphenol and when v is two, the alkylphenol is a dialkylphenol. Both mono- and dialkylphenols or mixtures thereof are suitable for use in the present invention, although monoalkylphenols are preferred. Most preferably, the alkylphenol of formula V is a monoalkylphenol having the alkyl group in the para position.

Numerous methods are known in the art for preparing the alkylphenols of formula V and any of these methods are suitable for use in the present invention. Generally, the alkylphenols of formula V are prepared by reacting an olefin or olefin mixture with phenol in the presence of an alkylation catalyst. Suitable alkylation catalysts include sulfonic acid catalysts, such as Amberlyst® 15, and Lewis acid catalysts, such as boron trifluoride etherate. The alkylation reaction is typically conducted at a temperature from about 25° C. to about 125° C. The reaction may be conducted in an essentially inert solvent or in the absence of a solvent. Examples of inert solvents include chlorobenzene and hexane.

Monoalkylphenols may be preferentially prepared by employing an excess of phenol in the alkylation reaction, typically 2 to 2.5 equivalents of phenol for each equivalent of olefin. The excess phenol is preferably recovered and recycled. Dialkylphenols may be preferentially prepared by employing a molar excess of olefin in the alkylation reaction, such as two or more equivalents of olefin per equivalent of phenol.

Preferred monoalkylphenols for use in the present invention include, for example, decylphenol, undecylphenol, dodecylphenol, tetradecylphenol, pentadecylphenol, hexadecylphenol, octadecylphenol, eicosylphenol, hexacosylphenol, triacontylphenol and the like. Also, mixtures of alkylphenols may be employed, such as a mixture of $C_{14}$—$C_{18}$ alkylphenols, a mixture of $C_{18}$—$_{24}$ alkylphenols, a mixture of $C_{20}$—$C_{24}$ alkylphenols, or a mixture of $C_{16}$—$C_{26}$ alkylphenols.

Particularly preferred alkylphenols are those derived from alkylation of phenol with polymers or oligomers of $C_3$ to $C_6$ olefins, such as polypropylene or polybutene. These polymers typically contain about 9 to about 100 carbon atoms, preferably about 10 to about 30 carbon atoms. An especially preferred alkylphenol is prepared by alkylating phenol with a propylene polymer having an average of 4 units. This polymer has the common name of propylene tetramer and is commercially available.

Alkylphenols derived from alpha olefin oligomers of $C_8$ to $C_{16}$ alpha olefins, such as the dimer, trimer and tetramer of decene, are also useful in this invention. Such alkylphenols are described in PCT International patent application Publication No. WO 90/07564, published Jul. 12, 1990, the disclosure of which is incorporated herein by reference.

The Alkyl Vinyl Ether Monomers

As described above, the first vinyl ether unit of the poly(vinyl ether) component is typically derived from a hydrocarbyl vinyl ether monomer. The subsequent units of the polymer are preferably derived from alkyl vinyl ether monomers having the formula:

$$R_5HC=CR_6-OR_9 \qquad (VI)$$

wherein $R_5$, $R_6$ and $R_9$ are as defined above. Preferably, $R_5$ and $R_6$ are each independently hydrogen or methyl. More preferably, $R_5$ and $R_6$ are both hydrogen.

The alkyl group $R_9$ can be a straight- or branched-chain alkyl group and preferably contains 1 to 6 carbon atoms, more preferably 2 to 4 carbon atoms. Particularly preferred alkyl groups are methyl, ethyl, n-propyl, isopropyl, n-butyl and isobutyl groups. Especially preferred alkyl groups are ethyl and isobutyl groups.

Suitable alkyl vinyl ethers include methyl vinyl ether ($H_2C=CH-O-CH_3$), ethyl vinyl ether, n-propyl vinyl ether, isopropyl vinyl ether, n-butyl vinyl ether, isobutyl vinyl ether and the like.

A number of suitable alkyl vinyl ether monomers are commercially available. Others can be readily prepared by the procedures discussed above for hydrocarbyl vinyl ether monomers. Alternatively, alkyl vinyl ether monomers can be produced on a commercial scale from alcohols and acetylene as described in Kirk-Othmer, *Encyclopedia of Chemical Technology*, 3rd Ed., Vol. 1, p. 269, Wiley-Interscience, New York (1983).

Polymerization Conditions

The poly(vinyl ether) component of the poly(vinyl ether) amines of this invention is preferably prepared by the living polymerization of a hydrocarbyl vinyl ether monomer and alkyl vinyl ether monomers. Living polymerization of vinyl ethers is well known in the art and is further described, for example, by T. Higashimura et al. in *Comprehensive Polymer Science*, Pergamon, Oxford, 1989, Vol. 3, Part I, Chapter 42 and references cited therein.

Living polymerization reactions employing vinyl ether monomers are typically conducted using an "initiating system" which comprises hydrogen iodide (HI) and a weak Lewis acid, such as zinc iodide ($ZnI_2$) or iodine ($I_2$). In the present invention, a hydrogen iodide/zinc iodide initiating system is particularly preferred. Other initiating systems may also be employed, such as a mixture of a halogenated aliphatic acid and a zinc salt of a halogenated aliphatic acid as described in U.S. Pat. No. 5,026,799, or the initiating systems described by M. Sawamoto et al. in *Makromol. Chem., Macromol. Symp.*, 1990, 32, 131 and references cited therein.

Generally, the living polymerization reaction will be conducted in a substantially anhydrous inert solvent at a temperature of about $-78°$ C. to about 50° C., preferably $-20°$ C. to 25° C. Suitable inert solvents include benzene, toluene, dichloromethane, diethyl ether and the like. Preferably, the polymerization reaction will be conducted under a dry inert gas atmosphere, such as nitrogen or argon, at about atmospheric or ambient pressure.

Typically, in the first step of the living polymerization reaction, a hydrocarbyl vinyl ether monomer of formula III is contacted with about 1.0 molar equivalents of hydrogen iodide to form an adduct according to the reaction:

$$R_1-(O-R_2)_m-O-C(R_4)=CHR_3 + HI \longrightarrow \qquad (3)$$

(III)

$$R_1-(O-R_2)_m-O-CI(R_4)-CH_2R_3$$

(VII)

wherein $R_{1-R4}$ and m are as defined above. Preferably, the hydrogen iodide is added as a solution in an inert solvent, such as hexane. This reaction is generally conducted for about 1.0 to about 20 minutes which is usually sufficient to result in the substantially complete conversion of the hydrocarbyl vinyl ether monomer to the adduct VII.

In the second step of the living polymerization reaction, an alkyl vinyl ether monomer of formula VI Or a mixture of such alkyl vinyl ether monomers is added to the solution containing the adduct VII, and subsequently, zinc iodide is introduced to initiate the polymerization reaction. Typically, a molar ratio of hydrogen iodide to zinc iodide ranging from about 5:1 to about 500:1, preferably about 50:1, will be employed.

Generally, the molar ratio of alkyl vinyl ether monomer to adduct VII will range from about 6:1 to about 100:1, preferably 11:1 to 51:1, more preferably 16:1 to 31:1. The alkyl vinyl ether monomer or mixture of monomers may be added entirely at the beginning of the polymerization reaction or may be added sequentially during the course of the reaction. By adding a mixture of alkyl vinyl ether monomers at the beginning of the reaction, a poly(vinyl ether) having an essentially random distribution of alkyl vinyl ether units can be produced. Alternatively, the sequential addition of different alkyl vinyl ether monomers produces a poly(vinyl ether) having substantial blocks of identical alkyl vinyl ether units.

The time employed for the polymerization reaction can vary over a wide range and will depend to some extent on the reaction temperature and on the vinyl ether monomers used in the polymerization process. Generally, the reaction will be conducted for about 0.25 to about 20 hours, preferably 1.0 to 2.0 hours or until essentially all the alkyl vinyl ether monomers have reacted to form polymer. Completion of the polymerization reaction can be monitored by observing the disappearance of the vinylic proton(s) from the alkyl vinyl ether monomers by $^1$H NMR, if desired.

When essentially all of the alkyl vinyl ether monomer has reacted to form polymer, the reactive terminal end of the polymer is quenched by contacting the reaction mixture with about 5 to about 20 equivalents of an aqueous alkali metal carbonate solution, such as aqueous potassium or sodium carbonate. This affords a carbonyl-terminated poly(vinyl ether) having the formula:

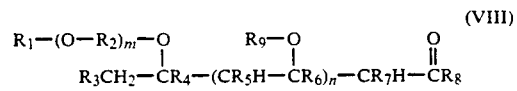

(VIII)

wherein $R_1$–$R_9$, m and n are as defined above. The quenching reaction is typically conducted at about $-20°$ C. to about $25°$ C. for about 0.1 to about 2 hours.

In a preferred method of preparing the poly(vinyl ether) amines of the present invention, the carbonyl group of the poly(vinyl ether) of formula VIII is reduced with a suitable reducing agent, such as a metal hydride reagent, to form a hydroxy-terminated poly(vinyl ether) having the formula:

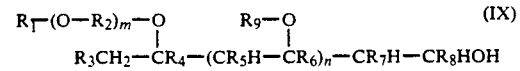

(IX)

wherein $R_1$–$R_9$, m and n are as defined above. A particularly preferred reducing agent is sodium borohydride.

Typically, the reduction reaction is effected by contacting the carbonyl-terminated poly(vinyl ether) of formula VIII with about 2 to about 10 molar equivalents of sodium borohydride in an essentially inert solvent. Suitable solvents include methanol, ethanol, propanol and the like. Ethanol is a particularly preferred solvent. The reaction is usually conducted at about 0° C. to about 40° C. for about 2 to about 24 hours. Other suitable methods for reducing carbonyl compounds to alcohols can be found, for example, in I. T. Harrison and S. Harrison, *Compendium of Organic Synthetic Methods,* pp. 81–84 and 111–118, Wiley-Interscience, New York (1971) and references cited therein.

The hydroxyl group of the poly(vinyl ether) of formula IX is then typically converted to an appropriate leaving group for coupling with a suitable amine component. For example, the hydroxyl group may be converted to a sulfonate, such as a methanesulfonate or a toluenesulfonate, by contacting the alcohol with a suitable sulfonyl chloride in an inert solvent, such as dichloromethane, in the presence of a suitable amine, such as triethylamine or pyridine, at a temperature in the range of about $-10°$ C. to about $30°$ C.

Alternatively, the hydroxyl group can be exchanged for a halogen by contacting the alcohol with a halogenating agent, such as thionyl chloride or oxalyl chloride, to form a halogen-terminated poly(vinyl ether). Other suitable methods for preparing sulfonates and halides from alcohols and appropriate reaction conditions for such reactions can be found, for example, in I.T. Harrison and S. Harrison, *Compendium of Orgnanic Synthetic Methods,* pp. 331–337, Wiley-Interscience, New York (1971) and references cited therein.

B. The Amine Component

As indicated above, the poly(vinyl ether) amines of the present invention contain an amine component which is covalently linked to the aforementioned poly(vinyl ether) component.

In general, the amine component will contain an average of at least about one basic nitrogen atom per molecule. A "basic nitrogen atom" is one that is titratable by a strong acid, for example, a primary, secondary or tertiary amine nitrogen. Preferably, at least one of the basic nitrogen atoms of the amine component will be primary or secondary amine nitrogen, more preferably at least one will be a primary amine nitrogen.

The amine component of the poly(vinyl ether) amines of this invention is preferably derived from ammonia ($NH_3$), a monoamine having 1 to about 8 carbon atoms, or a polyamine containing 2 to about 12 amine nitrogen atoms and from 2 to about 40 carbon atoms. Amine components derived from ammonia or a polyamine are particularly preferred, especially those derived from polyamines having a carbon-to-nitrogen ratio of from about 1:1 to 10:1.

In preparing the compounds of this invention using a polyamine where the various nitrogen atoms of the polyamine are not geometrically equivalent, several substitutional isomers are possible and each of these possible isomers is encompassed within this invention.

Suitable polyamines can have a straight- or branched-chain structure and may be cyclic or acyclic or combinations thereof. Generally, the amine nitrogen atoms of such polyamines will be separated from one another by at least two carbon atoms, i.e. polyamines having an aminal structure are not suitable. The polyamine may also contain one or more oxygen atoms, typically present as an ether or a hydroxyl group.

A particularly preferred group of polyamines for use in the present invention are polyalkylene polyamines, including alkylene diamines. Such polyalkylene polyamines will typically contain 2 to about 12 nitrogen atoms and 2 to about 24 carbon atoms. Preferably, the a)kylene groups of such polyalkylene polyamines will contain from 2 to about 6 carbon atoms, more preferably from 2 to 4 carbon atoms.

Examples of suitable polyalkylene polyamines include ethylenediamine, propylenediamine, isopropylenediamine, butylenediamine, pentylenediamine, hexylenediamine, diethylenetriamine, dipropylenetriamine, diisopropylenetriamine, dibutylenetriamine, di-sec-butylenetriamine, triethylenetetraamine, tripropylenetetraamine, triisobutylenetetraamine, tetraethylenepentamine, pentaethylenehexamine and mixtures thereof.

Particularly suitable polyalkylene polyamines are those having the formula:

$$H_2N-(R_{10}NH)_y-H \qquad (X)$$

wherein $R_{10}$ is a straight- or branched-chain alkylene group having 2 to about 6 carbon atoms, preferably 2 to 4 carbon atoms, most preferably 2 carbon atoms, i.e. ethylene ($-CH_2CH_2-$); and y is an integer from 1 to 3, preferably 1 or 2.

Particularly preferred polyalkylene polyamines are ethylenediamine, diethylenetriamine and triethylenetetraamine. Most preferred is ethylenediamine.

Also contemplated for use in the present invention are cyclic polyamines having one or more 5- to 6-membered rings. Such cyclic polyamines compounds include piperazine, 2-methylpiperazine, N-(2-aminoethyl)piperazine, N-(2-hydroxyethyl)piperazine, 1,2-bis-(N-piperazinyl)ethane, 3-aminopyrrolidine, N-(2-aminoethyl)pyrrolidine and the like. Among the cyclic polyamines, the piperazines are preferred.

Alternatively, the amine component may be derived from ammonia or a monoamine having 1 to about 8 carbon atoms. Suitable monoamines include primary N-alkylamines and secondary N,N-dialkylamines. Among the monoamines, primary N-alkylamines having an unbranched alkyl group containing 1 to about 4 carbon atoms are preferred, such as methylamine, ethylamine, n-propylamine, and n-butylamine. Most preferred among the monoamines is methylamine.

Many of the amines suitable for use in present invention are commercially available and others many be prepared by methods which are well known in the art. For example, methods for preparing amines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99–116.

The poly(vinyl ether) amines of the present invention are generally prepared by contacting the amine component with an end-functionalized poly(vinyl ether) component having a suitable leaving group, such as a sulfonate or halogen as described above, at a temperature in the range of about 25° C. to about 175° C. for about 1 to about 24 hours.

Generally, a molar ratio of amine component to poly(vinyl ether) component ranging from about 2:1 to about 20:1, preferably 5:1 to 10:1, will be employed. The reaction will typically be conducted at atmospheric pressure, however, when employing a lower-boiling amine component, such as ammonia, higher pressures may be preferred. The desired product may be obtained by washing the reaction mixture with water and stripping the mixture, usually under vacuum, to remove any residual solvent.

Alternatively, the poly(vinyl ether) amines of the present invention may be prepared from a carbonyl-terminated poly(vinyl ether) of formula VIII and an amine component using standard reductive amination procedures.

Fuel Compositions

The poly(vinyl ether) amines of the present invention are useful as additives in hydrocarbon fuels to prevent and control engine deposits, particularly intake valve deposits. Typically, the desired deposit control will be achieved by operating an internal combustion engine with a fuel composition containing a poly(vinyl ether) amine of the present invention. The proper concentration of additive necessary to achieve the desired deposit control varies depending upon the type of fuel employed, the type of engine, and the presence of other fuel additives.

In general, the concentration of the poly(vinyl ether) amines of this invention in hydrocarbon fuel will range from about 50 to about 2500 parts per million (ppm) by weight, preferably from 75 to 1,000 ppm. When other deposit control additives are present, a lesser amount of the present additive may be used. Furthermore, lower concentrations of, for example, 30 to 70 ppm may be preferred when the present additives are employed as carburetor detergents only.

The poly(vinyl ether) amines of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will be generally range from about 10 to about 70 weight percent, preferably 10 to 50 weight percent, more preferably from 10 to 25 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl(polyoxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the poly(vinyl ether) amines of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis.

These Carrier fluids are believed to act as a carrier for the fuel additives of the present invention and to assist in removing and retarding deposits. The carrier fluid may also exhibit synergistic deposit control properties when used in combination with the poly(vinyl ether) amines of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 2:1 to 5:1, most preferably about 4:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof and should not be interpreted as limitations upon the scope of the invention.

EXAMPLE 1

Preparation of 2-(p-Dodecylohenoxy)ethyl Vinyl Ether

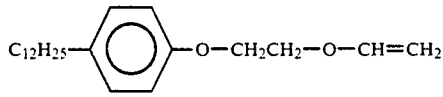

To a flask equipped with a mechanical stirrer, reflux condenser, addition funnel, thermometer and nitrogen inlet was added 104.96 grams of p-dodecylphenol (prepared by alkylating phenol with propylene tetramer), 120 mL of anhydrous dimethylsulfoxide and 24 grams of sodium hydroxide. The mixture was stirred at room temperature for 30 minutes and then heated to 70-75° C. with a heating mantle for 2 hours. The heating mantle was removed and 64 grams of 2-chloroethyl vinyl ether were added dropwise at a rate to maintain the temperature below 80° C. After the addition was complete, the reaction was heated to 75° C. for 16 hours, cooled to room temperature and poured into 500 mL of water. The water was extracted three times with diethyl ether and the combined organic layers were washed three times with water and once with saturated aqueous sodium chloride solution. The organic layer was then dried over anhydrous sodium sulfate, filtered and the solvents removed in vacuo to yield 132.2 grams of the desired ether as an orange oil.

EXAMPLE 2

Preparation of

α-(Formylmethyl)-ω-[1-(2'-(p-dodecylphenoxy)ethoxy)ethyl]poly(1-ethoxyethylene)

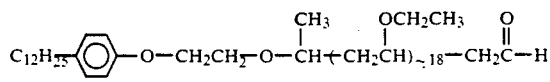

To an oven-dried flask equipped with a thermometer, magnetic stirrer, septa, addition funnel and nitrogen inlet was added 37.5 grams of 2-(p-dodecylphenoxy)ethyl vinyl ether from Example 1 and 3 L of anhydrous toluene. The contents of the flask were cooled to −10° C. and 256.4 mL of anhydrous 0.44N hydrogen iodide in hexane were added at a rate to maintain the temperature below −10° C. The reaction was stirred at −10° C. for 10 minutes and 204.8 mL of ethyl vinyl ether (previously distilled from calcium hydride and then distilled from sodium) were added followed by 0.72 grams of anhydrous zinc iodide dissolved in 11.3 mL of anhydrous diethyl ether. The zinc iodide solution was added at a rate to maintain the temperature at −10° C. The reaction mixture was stirred at −10° C. for 1.5 hours, then quenched with an aqueous solution of potassium carbonate (155.94 grams dissolved in 624 mL of water) and stirred for 15 minutes. A 10% aqueous sodium thiosulfate solution (500 mL) was added and the cooling bath was removed. The organic layer was separated and washed twice with 10% aqueous sodium thiosulfate, three times with water and once with saturated aqueous sodium chloride. The organic layer was then dried over anhydrous sodium sulfate, filtered and the solvents removed in vacuo to yield 195.40 grams of the desired aldehyde.

EXAMPLE 3

Preparation of α-(2-Hydroxyethyl)-ω-[1-(2'-(p-dodecylohenoxy)ethoxy)ethyl]poly(1-ethoxyethylene)

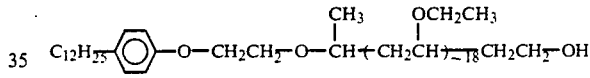

Sodium borohydride (21.9 grams) was added to a solution of 195.4 grams of the aldehyde from Example 2 dissolved in 1 L of ethanol under nitrogen. The reaction was stirred at room temperature for 16 hours and 300 mL of 10% aqueous sodium hydroxide were added. Most of the solvent was removed in vacuo and 1.16 L of 10% aqueous sodium hydroxide were added. The aqueous layer was extracted four times with hexane. The combined organic layers were washed once with saturated aqueous sodium chloride, dried over anhydrous sodium sulfate, filtered and the solvents removed in vacuo to yield 184.36 grams of the desired alcohol.

EXAMPLE 4

Preparation of α-(2-Methanesulfonyloxyethyl)-ω-[1-(2'-(p-dodecylphenoxy)ethoxy)ethyl]poly(1-ethoxvethylene)

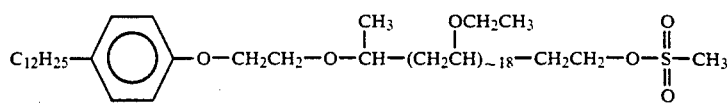

Triethylamine (18.3 mL) was added to a solution of 184.36 grams of the alcohol from Example 3 dissolved in 1.8 L of anhydrous dichloromethane. The contents were cooled to 0° C. and 9.3 mL of methanesulfonyl chloride were added dropwise. The cooling bath was removed and the reaction was stirred at room temperature for 6 hours. The reaction was diluted with 1 L of dichloromethane and the resulting solution was washed twice with saturated aqueous sodium bicarbonate and once with saturated aqueous sodium chloride solution. The organic layer was dried over anhydrous sodium sulfate, filtered and the solvents removed in vacuo to yield 227.7 grams of the desired mesylate.

EXAMPLE 5

Preparation of
α-[2-N-(2'-Aminoethyl)aminoethyl]-ω-[1-(2-(p-dodecylphenoxy)ethoxy)ethy]poly(1-ethoxyethylene)

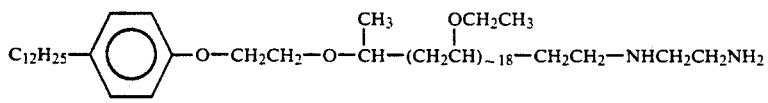

The mesylate (227.7 grams) from Example 4 and 644 mL of ethylenediamine were heated at reflux for 16 hours. The reaction was diluted with 3 L of hexane and the resulting solution was washed twice with saturated aqueous sodium bicarbonate and twice with water. The organic layer was dried over anhydrous sodium sulfate, filtered and the solvent removed in vacuo to give an oil. The oil was chromatographed on silica gel, eluting first with dichloromethane/isopropanol/ammonium hydroxide (9:0.9:0.1) and then With hexane/diethyl ether/methanol/isopropylamine (4:4:1.5:0.5) to yield 82.6 grams of the desired product as a yellow oil. The product had an average of 18 ethoxyethylene units. $^1$H NMR (CDCl$_3$) δ7.05-7.25 (m, 24), 6.7-6.9 (m, 2H), 3.95-4.05 (m, 2H), 3.1-3.9 (m, 57H), 2.6-2.9 (m, 6H), 0.4-1.95 (m, 120H).

EXAMPLE 6

Preparation of
α-(Formylmethyl)-ω-[1-(2'-(p-dodecylphenoxy)ethoxy)ethy]poly(1-isobutoxyethylene)

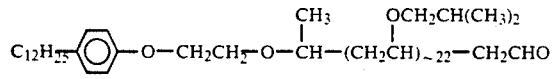

To an oven-dried flask equipped with a thermometer, magnetic stirrer, septa, addition funnel and nitrogen inlet was added 18.75 grams of 2-(p-dodecylphenoxy)ethyl vinyl ether from Example 1 and 1.5 L of anhydrous toluene. The contents of the flask were cooled to −10° C. and 110.6 mL of anhydrous 0.51N hydrogen iodide in hexane were added at a rate to maintain the temperature below −10° C. The reaction was stirred at −10° C. for 10 minutes and 138.7 mL of isobutyl vinyl ether (distilled from calcium hydride and then distilled from sodium) were added followed by 0.36 grams of anhydrous zinc iodide dissolved in 5.7 mL of anhydrous diethyl ether. The zinc iodide was added at a rate to maintain the temperature at −10° C. The reaction mixture was stirred at −10° C. for 1.5 hours and then 77.97 grams of potassium carbonate dissolved in 312 mL of water were added. The reaction was stirred for 15 minutes and then 300 mL of 10% aqueous sodium thiosulfate were added followed by removal of the cooling bath. The organic layer was separated and washed twice with 10% aqueous sodium thiosulfate, three times with water and once with saturated aqueous sodium chloride. The organic layer was then dried over anhydrous sodium sulfate, filtered and the solvents removed in vacuo to yield 125.01 grams of the desired aldehyde.

EXAMPLE 7

Preparation of
α-(2-Hydroxyethyl)-ω-[1-(2'-(p-dodecylohenoxy)ethoxy)ethyl]poly(1-isobutoxyethylene)

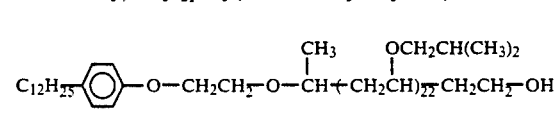

Sodium borohydride (10.87 grams) was added to a solution of 125.01 grams of the aldehyde from Example 6 dissolved in 663 mL of ethanol under nitrogen. The reaction was stirred at room temperature for 16 hours and 192 mL of 10% aqueous sodium hydroxide were added. Most of the solvent was removed in vacuo and 744 mL of 10% aqueous sodium hydroxide were added. The aqueous layer was extracted four times with hexane. The combined organic layers were washed once with saturated aqueous sodium chloride, dried over anhydrous sodium sulfate, filtered and the solvents removed in vacuo to yield 124.97 grams of the desired alcohol.

EXAMPLE 8

Preparation of
α-(2-Methanesulfonyloxyethyl)-ω-[1-(2'-(p-dodecylphenoxy)ethoxy)ethyl]poly(1-isobutoxyethylene)

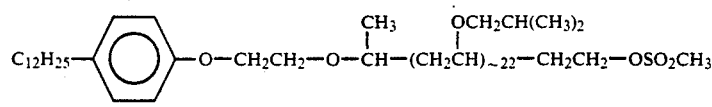

Triethylamine (9.6 mL) was added to a solution of 124.97 grams of the alcohol from Example 7 dissolved in 1.22 L of anhydrous dichloromethane. The contents were cooled to 0° C. and 4.9 mL of methanesulfonyl chloride were added dropwise. The cooling bath was removed and the reaction was stirred at room temperature for 6 hours. The reaction was diluted with 1 L of dichloromethane and the resulting solution was washed twice with saturated aqueous sodium bicarbonate and once with saturated aqueous sodium chloride. The organic layer was dried over anhydrous sodium sulfate, filtered and the solvents removed in vacuo to yield 135.38 grams of the desired mesylate.

EXAMPLE 9

Preparation of
α-[2-N-(2'-Aminoethyl)aminoethyl]-ω-[1-(2'-(p-dodecylphenoxy)ethoxy)ethyl]poly(1-isobutoxyethylene)

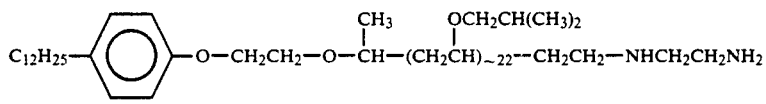

The mesylate (135.38 grams) from Example 8 and 382.9 mL of ethylenediamine were heated at reflux for 16 hours. The reaction was diluted with 2 L of hexane and the resulting solution was washed twice with saturated aqueous sodium bicarbonate and twice with water. The organic layer was dried over anhydrous sodium sulfate, filtered and the solvent removed in vacuo to give an oil. The oil was chromatographed on silica gel, eluting first with dichloromethane/isopropanol/ammonium hydroxide (9:0.9:0.1) and then With hexane/diethyl ether/methanol/isopropylamine (4:4:1.5:0.5) to yield 27.5 grams of the desired product as a yellow oil The product had an average of 22 isobutoxyethylene units. $^1$H NMR (CDCl$_3$) δ 7.05-7.25 (m, 2H), 6.7-6.9 (m, 2H), 4.05-4.15 (t, 2H), 2.8-4.0 (m, 69H), 2.6-1.8 (m, 6H), 0.6-2.0 (m, 228H).

EXAMPLE 10

Preparation of
α-(1-Formylethyl)-ω-[1-(2'-(p-dodecylohenoxy)ethoxy)ethyl]poly(1-ethoxypropylene)

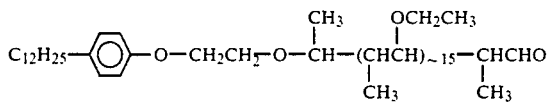

To an oven-dried flask equipped with a thermometer, magnetic stirrer, septa, addition funnel and nitrogen inlet was added 18.75 grams of 2-(p-dodecylphenoxy)ethyl vinyl ether from Example 1 and 1.5 L of anhydrous toluene. The contents of the flask Were cooled to a −10° C. and 110.6 mL of anhydrous 0.5N hydrogen iodide in hexane were added at a rate to maintain the temperature below −10° C. The reaction was stirred at −10° C. for 10 minutes and 92.3 mL of ethyl 1-propenyl ether (distilled from calcium hydride and then distilled from sodium) were added followed by 0.36 grams of anhydrous zinc iodide dissolved in 5.7 mL of anhydrous diethyl ether. The zinc iodide solution was added at a rate to maintain the temperature at −10° C. The reaction mixture was stirred at −10° C. for 1.5 hours and 77.97 grams of potassium carbonate dissolved in 312 mL of water were added. The reaction was stirred for 15 minutes and 300 mL of 10% aqueous sodium thiosulfate were added followed by removal of the cooling bath. The organic layer was separated and washed twice with 10% aqueous sodium thiosulfate, three times with water and once with saturated aqueous sodium chloride. The organic layer was then dried over anhydrous sodium sulfate, filtered and the solvents removed in vacuo to yield 670.72 grams of the desired aldehyde.

EXAMPLE 11

Preparation of
α-(2-Hydroxy-1-methylethyl)-ω-[1-(2'-(p-dodecylphenoxy)ethoxy)ethy]poly(1-ethoxypropylene)

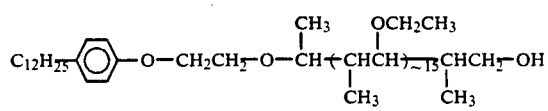

Sodium borohydride (6.10 grams) was added to a solution of 70.72 grams of the aldehyde from Example 10 dissolved in 362 mL ethanol under nitrogen. The reaction was stirred at room temperature for 16 hours and 110 mL of 10% aqueous sodium hydroxide were added. Most of the solvent was removed in vacuo and 421 mL of 10% aqueous sodium hydroxide was added. The aqueous layer was extracted four times with hexane. The combined organic layers were washed once with saturated aqueous sodium chloride, dried over anhydrous sodium sulfate, filtered and the solvents removed in vacuo to yield 80.46 grams of the desired alcohol.

EXAMPLE 12

Preparation of
α-(2-Methanesulfonyloxy-1-methylethyl)-ω-[1-(2'-(p-dodecylphenoxy)ethoxy)ethyl]poly(1-ethoxypropylene)

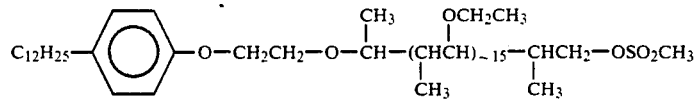

Triethylamine (6.1 mL) was added to a solution of 80.46 grams of the alcohol from Example 11 dissolved in 785 mL of anhydrous dichloromethane. The contents were cooled to 0° C. and 3.1 mL of methanesulfonyl chloride were added dropwise. The cooling bath was removed and the reaction was stirred at room temperature for 6 hours. The reaction was diluted with 500 mL of dichloromethane and the resulting solution was washed twice with saturated aqueous sodium bicarbonate and once with saturated aqueous sodium chloride solution. The organic layer was dried over anhydrous sodium sulfate, filtered and the solvents removed in vacuo to yield 81.2 grams of the desired mesylate.

EXAMPLE 13

Preparation of
α-[2-N-(2'-Aminoethyl)amino-1-methylethyl]-ω-[1-(2'-(p-dodecylphenoxy)ethoxy)ethyl]poly(1-ethoxypropylene)

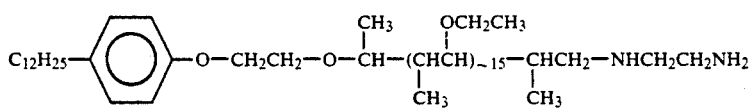

The mesylate (81.2 grams) from Example 12 and 230 mL of ethylenediamine were heated at reflux for 16 hours. The reaction was diluted with 800 mL of hexane and the resulting solution washed twice with saturated aqueous sodium bicarbonate and twice with water. The organic layer was dried over anhydrous sodium sulfate, filtered and the solvent removed in vacuo to give an oil. The oil was chromatographed on silica gel, eluting first with dichloromethane and then with hexane/diethyl ether/methanol/isopropylamine (4:4:1.5:0.5) to yield 8.32 grams of the desired product as a yellow oil. The product had an average of 15 1-ethoxypropylene units.
$^1$H NMR (CDCl$_3$) δ7.05–7.25 (m, 2H), 6.7–6.9 (m, 2H), 4.0–4.1 (t, 2H), 2.8–4.0 (m, 48H), 2.4–2.8 (m, 6H), 0.5–2.2 (m, 137H).

EXAMPLE 14

Thermogravimetric Analysis

The thermal stability of various test samples was measured by thermogravimetric analysis (TGA). The TGA procedure employed a DuPont 951 TGA instrument coupled with a microcomputer for data analysis. Samples of the fuel additive (approximately 25 milligrams) were heated from 25° C. to 700° C. at 10° C. per minute under air flowing at 100 cubic centimeters per minute. The temperature at which 95% weight loss occurred for each of the test samples was recorded and is shown in Table I. A higher 95% weight loss temperature indicates superior thermal stability.

TABLE I

| Thermogravimetric Analysis Results | |
|---|---|
| Sample | 95% Weight Loss Temperature |
| Example 5 | 533° C. |
| Example 9 | 488° C. |
| Example 13 | 485° C. |
| Comparative Example A[1] | 340° C. |
| Comparative Example B[2] | 331° C. |

[1]Comparative Example A was a dodecylphenyl poly(oxybutylene) ethylenediamine (having a molecular weight of about 1690) prepared in a manner similar to that described in Example 6 of U.S. Pat. No. 4,247,301 to Honnen.
[2]Comparative Example B was a dodecylphenyl poly(oxybutylene) ethylenediamine carbamate (having a molecular weight of about 1718) prepared in a manner similar to that described in Examples 6–8 of U.S. Pat. No. 4,160,648 to Lewis et al.

The data in Table I demonstrates that the poly(vinyl ether) amines of the present invention (Examples 5, 9, and 13) have significantly increased thermal stability (>145° C.) compared to known poly (oxyalkylene) fuel additives.

EXAMPLE 15

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table II.

TABLE II

| Single-Cylinder Engine Test Results | | | |
|---|---|---|---|
| | Intake Valve Deposit Weight (in milligrams) | | |
| Sample [1] | Run 1 | Run 2 | Average |
| Base Fuel | 197.4 | 212.3 | 204.9 |
| Example 5 | 1.8 | 1.1 | 1.5 |
| Example 9 | 9.0 | 8.2 | 8.6 |
| Example 13 | 126.1 | 116.7 | 121.4 |

[1]At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table II illustrates the significant reduction in intake valve deposits provided by the poly(vinyl ether) amines of the present invention (Examples 5, 9, and 13) compared to the base fuel.

What is claimed is:

1. A compound of the formula:

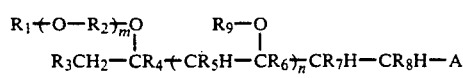

wherein
A is an amine moiety having at least one basic nitrogen atom;
$R_1$ is a hydrocarbyl group having a sufficient number of carbon atoms to render said compound soluble in hydrocarbons boiling in the gasoline or diesel fuel range;
$R_2$ alkylene having 2 to about 8 carbon atoms;
$R_3$, $R_4$, $R_5$, $R_6$, $R_7$ and $R_8$ are each independently hydrogen or lower alkyl having 1 to about 4 carbon atoms;
$R_9$ is alkyl having 1 to about 10 carbon atoms;
m is 0 or 1; and n is an integer from 5 to 99.

2. The compound according to claim 1 wherein n is an integer from 10 to 50.

3. The compound according to claim 2 wherein n is an integer from 15 to 30.

4. The compound according to claim 2 wherein said amine moiety is derived from ammonia, a monoamine having 1 to about 8 carbon atoms, or a polyamine containing 2 to about 12 amine nitrogen atoms and from 2 to about 40 carbon atoms.

5. The compound according to claim 4 wherein $R_1$ is alkyl having 8 to about 120 carbon atoms or alkylphenyl having an alkyl group containing 4 to about 100 carbon atoms.

6. The compound according to claim 5 wherein $R_2$ is alkylene having 2 to 4 carbon atoms; $R_3$, $R_4$, $R_5$, $R_6$, $R_7$ and $R_8$ are each independently hydrogen, methyl, or ethyl; and $R_9$ is alkyl having 1 to 6 carbon atoms.

7. The compound according to claim 6 wherein said amine moiety is derived from a polyalkylene polyamine containing 2 to about 12 nitrogen atoms and 2 to about 24 carbon atoms.

8. The compound according to claim 7 wherein $R_1$ is alkyl having 10 to 30 carbon atoms or alkylphenyl having an alkyl group containing 10 to 30 carbon atoms.

9. The compound according to claim 8 wherein $R_2$ is ethylene; $R_3$, $R_4$, $R_5$, $R_6$, $R_7$ and $R_8$ are each hydrogen; and $R_9$ is alkyl having 2 to 4 carbon atoms.

10. The compound according to claim 9 wherein said polyalkylene polyamine has the formula:

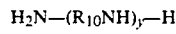

wherein $R_{10}$ is alkylene having 2 to about 6 carbon atoms and y is an integer from 1 to 3.

11. The compound according to claim 8 wherein $R_{10}$ is ethylene.

12. The compound according to claim 11 wherein y is 1 or 2.

13. The compound according to claim 11 wherein $R_1$ is alkylphenyl having an alkyl group containing 12 to 24 carbon atoms.

14. The compound according to claim 13 wherein said alkyl group is derived from propylene tetramer.

15. The compound according to claim 14 wherein $R_9$ is ethyl or isobutyl.

16. The compound according to claim 15 wherein m is 1.

17. A fuel composition comprising a major amount of hydrocarbons boiling in the gasoline or diesel range and an effective detergent amount of a compound of the formula:

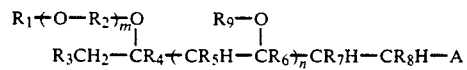

wherein
  A is an amine moiety having at least one basic nitrogen atom;
  $R_1$ is a hydrocarbyl group having a sufficient number of carbon atoms to render said compound soluble in hydrocarbons boiling in the gasoline or diesel fuel range;
  $R_2$ is an alkylene group having 2 to about 8 carbon atoms;
  $R_3$, $R_4$, $R_5$, $R_6$, $R_7$ and $R_8$ are each independently hydrogen or a lower alkyl group having 1 to about 4 carbon atoms;
  $R_9$ is a straight- or branched-chain alkyl group having 1 to about 10 carbon atoms;
  m is 0 or 1; and n is an integer from 5 to 99.

18. The fuel composition according to claim 17 wherein said amine moiety is derived from ammonia, a monamine having 1 to about 8 carbon atoms, or a polyamine containing 2 to about 12 amine nitrogen atoms and from 2 to about 40 carbon atoms; $R_1$ is alkyl having 8 to about 120 carbon atoms or alkylphenyl having an alkyl group containing 4 to about 100 carbon atoms; and n is an integer from 10 to 50.

19. The fuel composition according to claim 18 wherein $R_2$ is alkylene having 2 to 4 carbon atoms; $R_3$, $R_4$, $R_5$, $R_6$, $R_7$ and $R_8$ are each independently hydrogen, methyl, or ethyl; and $R_9$ is alkyl having 1 to 6 carbon atoms.

20. The fuel composition according to claim 19 wherein said amine moiety is derived from a polyalkylene polyamine containing 2 to about 12 nitrogen atoms and 2 to about 24 carbon atoms; and $R_1$ is alkyl having 10 to 30 carbon atoms or alkylphenyl having an alkyl group containing 10 to 30 carbon atoms.

21. The fuel composition according to claim 20 wherein $R_2$ is ethylene; $R_3$, $R_4$, $R_5$, $R_6$, $R_7$ and $R_8$ are each hydrogen; and $R_9$ is alkyl having 2 to 4 carbon atoms.

22. The fuel composition according to claim 21 wherein said polyalkylene polyamine has the formula:

wherein $R_{10}$ is alkylene having 2 to about 6 carbon atoms and y is an integer from 1 to 3.

23. The fuel composition according to claim 22 wherein $R_{10}$ is ethylene.

24. The fuel composition according to claim 23 wherein y is 1 or 2.

25. The fuel composition according to claim 17 wherein said composition contains about 50 to about 2500 parts per million by weight of said compound.

26. The fuel composition according to claim 25 wherein said composition contains about 100 to about 5000 parts per million by weight of a fuel-soluble, non-volatile carrier fluid.

27. A method for reducing engine deposits in an internal combustion engine comprising operating said engine with the fuel composition of claim 17.

28. A fuel concentrate comprising an inert stable oleophilic organic solvent boiling in the range of from about 150° F. to 400° F. and from about 10 to about 70 weight percent of a compound of the formula:

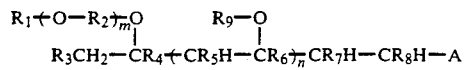

wherein
  A is an amine moiety having at least one basic nitrogen atom;
  $R_1$ is a hydrocarbyl group having a sufficient number of carbon atoms to render said compound soluble in hydrocarbons boiling in the gasoline or diesel fuel range;
  $R_2$ is an alkylene group having 2 to about 8 carbon atoms;
  $R_3$, $R_4$, $R_5$, $R_6$, $R_7$ and $R_8$ are each independently hydrogen or a lower alkyl group having 1 to about 4 carbon atoms;
  $R_9$ is a straight- or branched-chain alkyl group having 1 to about 10 carbon atoms;
  m is 0 or 1; and n is an integer from 5 to 99.

29. The fuel concentrate according to claim 28 wherein said amine moiety is derived from ammonia, a monoamine having 1 to about 8 carbon atoms; or a polyamine containing 2 to about 12 amine nitrogen atoms and from 2 to about 40 carbon atoms; $R_1$ is alkyl having 8 to about 120 carbon atoms or alkylphenyl having an alkyl group containing 4 to about 100 carbon atoms; and n is an integer from 10 to 50.

30. The fuel concentrate according to claim 29 wherein $R_2$ is alkylene having 2 to 4 carbon atoms; $R_3$, $R_4$, $R_5$, $R_6$, $R_7$ and $R_8$ are each independently hydrogen, methyl, or ethyl; and $R_9$ is alkyl having 1 to 6 carbon atoms.

31. The fuel concentrate according to claim 30 wherein said amine moiety is derived from a polyalkylene polyamine containing 2 to about 12 nitrogen atoms and 2 to about 24 carbon atoms; and $R_1$ is alkyl having 10 to 30 carbon atoms or alkylphenyl having an alkyl group containing 10 to 30 carbon atoms.

32. The fuel concentrate according to claim 31 wherein $R_2$ is ethylene; $R_3$, $R_4$, $R_5$, $R_6$, $R_7$ and $R_8$ are each hydrogen; and $R_9$ is alkyl having 2 to 4 carbon atoms.

33. The fuel concentrate according to claim 32 wherein said polyalkylene polyamine has the formula:

$$H_2N-(R_{10}NH)_y-H$$

wherein $R_{10}$ is alkylene having 2 to about 6 carbon atoms and y is an integer from 1 to 3.

34. The fuel concentrate according to claim 33 wherein $R_{10}$ is ethylene.

35. The fuel concentrate according to claim 34 wherein y is 1 or 2.

36. The fuel concentrate according to claim 28 wherein said concentrate contains 10 to 50 weight percent of said compound.

37. The fuel concentrate of claim 28 wherein said concentrate contains about 20 to about 60 weight percent of a fuel-soluble, nonvolatile carrier fluid.

* * * * *